United States Patent [19]

Schulze et al.

[11] 4,022,214

[45] May 10, 1977

[54] METHOD OF TREATING SUBSTANCES IN AN AMBIENT ENVIRONMENT WITH A CRYOGENIC MATERIAL

[75] Inventors: Robert R. Schulze, Des Moines; Floyd R. Ladd, West Des Moines, both of Iowa

[73] Assignee: Robert R. Schulze, Des Moines, Iowa

[22] Filed: Feb. 9, 1976

[21] Appl. No.: 656,349

Related U.S. Application Data

[62] Division of Ser. No. 570,723, April 23, 1975.

[52] U.S. Cl. ............................................. 128/303.1
[51] Int. Cl.[2] ........................................ A61B 17/36
[58] Field of Search ............ 62/55, 293; 128/303.1; 141/113

[56] References Cited

UNITED STATES PATENTS

| | | | |
|---|---|---|---|
| 2,536,001 | 12/1950 | Chase | 62/293 |
| 2,746,264 | 5/1956 | Keyes | 128/303.1 UX |
| 3,421,508 | 1/1969 | Nestrock | 128/303.1 |
| 3,425,417 | 2/1969 | Kanbar et al. | 62/293 X |
| 3,800,552 | 4/1974 | Sollami et al. | 128/303.1 X |

FOREIGN PATENTS OR APPLICATIONS 141,040  10/1930  Switzerland .......................... 62/293

*Primary Examiner*—Channing L. Pace
*Attorney, Agent, or Firm*—Zarley, McKee, Thomte, Voorhees & Sease

[57] ABSTRACT

A method of treating substances in an ambient environment with a cryogenic material is disclosed comprising a barrel having a plunger mechanism movably mounted therein and having a valve on the lower end thereof. The valve normally closes the lower end of the barrel but the plunger may be moved relative to the barrel to permit cryogenic liquid such as liquid nitrogen to bypass the valve and to move upwardly into the interior of the barrel. The valve has a tip portion at the lower end thereof. The barrel is removably positioned in a guard so that the tip portion extends outwardly through the bottom of the guard and so that the upper end of the plunger is exposed above the guard. The tip portion has a lower end portion which is extremely thin so that the cryogenic liquid will be positioned closely adjacent the skin but not in actual contact therewith when the tip portion is placed into contact with the patient's skin. The method of charging the device is disclosed as is the method of using the same.

1 Claim, 8 Drawing Figures

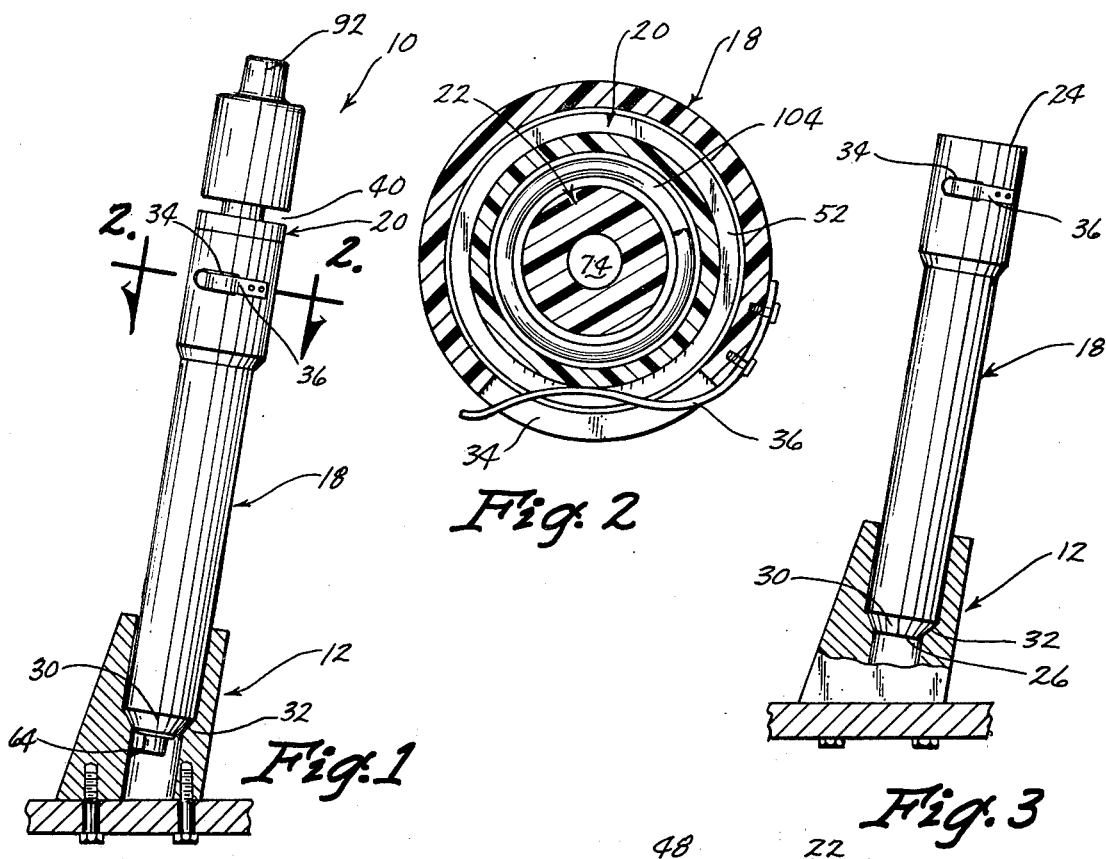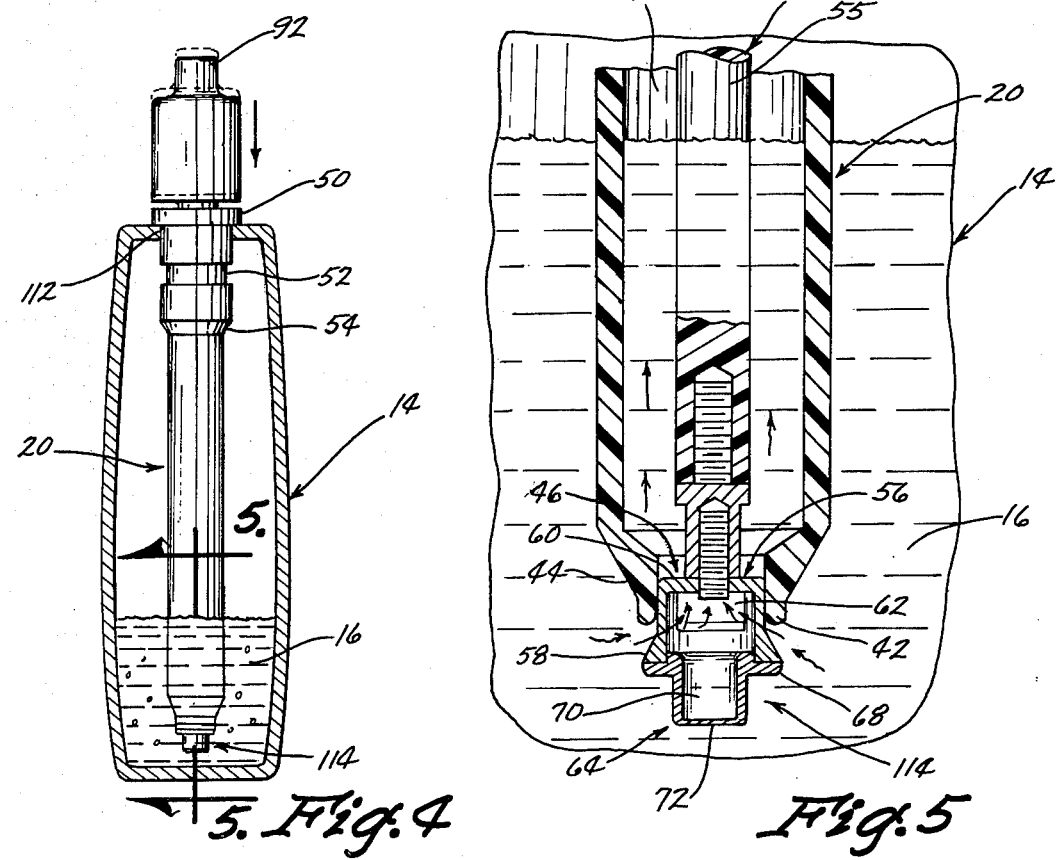

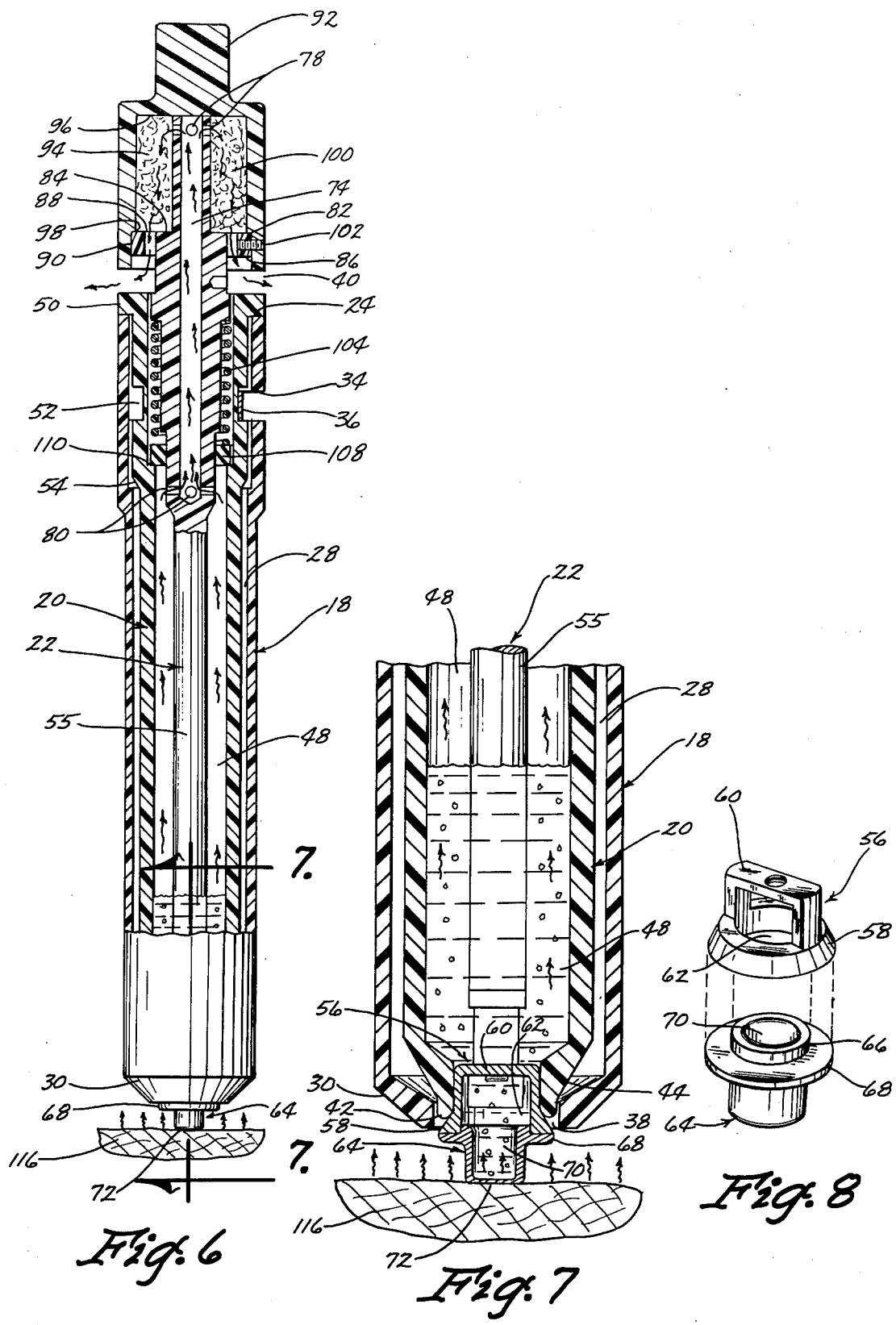

METHOD OF TREATING SUBSTANCES IN AN AMBIENT ENVIRONMENT WITH A CRYOGENIC MATERIAL

BACKGROUND OF THE INVENTION

This invention relates to a device which may be used with liquid nitrogen or the like for freezing areas on the skin such as warts, etc.

Liquid nitrogen or other cryogenic liquids are frequently used in the treatment of or in removing warts or the like from a person's skin. One method of removing a wart or the like is to immerse a wick-like device in liquid nitrogen having a temperature of approximately −335° Fahrenheit. The wick is then placed in contact with the wart or the like to "burn" by freezing the wart. The problem exists in such a method in that the liquid nitrogen quickly vaporizes which permits the wick to only treat the area for approximately one or two seconds prior to the liquid nitrogen vaporizing.

Therefore, it is a principal object of the invention to provide an improved cryogenic probe.

A further object of the invention is to provide a cryogenic probe which may be used to freeze areas of the skin wherein the liquid nitrogen or the like is positioned closely adjacent the skin but not in actual contact therewith.

A further object of the invention is to provide a cryogenic probe which permits areas of the skin to be treated for approximately one minute.

A further object of the invention is to provide a cryogenic probe wherein areas of the skin may be treated and wherein the heat of the skin permits the utilization of the heat of evaporation of the liquid nitrogen.

A further object of the invention is to provide a method of charging a cryogenic probe.

A further object of the invention is to provide a method of treating areas of the skin employing a cryogenic probe.

A further object of the invention is to provide a cryogenic probe which is economical of manufacture, durable in use and refined in appearance.

These and other objects will be apparent to those skilled in the art.

BRIEF DESCRIPTION OF THE DRAWINGS

This invention consists in the construction, arrangements and combination of the various parts of the device, whereby the objects contemplated are attained as hereinafter more fully set forth, specifically pointed out in the claims, and illustrated in the accompanying drawings, in which:

FIG. 1 is a side view of the cryogenic probe of this invention:

FIG. 2 is an enlarged sectional view seen on lines 2—2 of FIG. 1:

FIG. 3 is a view similar to FIG. 1 except that the inner portion of the probe has been removed from the outer portion thereof:

FIG. 4 is a side view illustrating the inner member of the probe being inserted in a cryogenic liquid container:

FIG. 5 is an enlarged sectional view seen on lines 5—5 of FIG. 4:

FIG. 6 is a partial longitudinal sectional view of the probe illustrating the tip thereof being in contact with the skin of a patient:

FIG. 7 is an enlarged sectional view seen lines 7—7 of FIG. 6; and

FIG. 8 is an exploded perspective view of the valve tip.

DESCRIPTION OF THE PREFERRED EMBODIMENT

The cryogenic probe of this invention is referred to generally by the reference numeral 10 while the reference numeral 12 refers to a support adapted to support the probe 10. The numeral 14 refers generally to a vacuum bottle container or the like adapted to contain a cryogenic liquid 16 such as nitrogen. Probe 10 generally comprises an outer guard 18, barrel 20 and plunger 22.

For purposes of description, guard 18 will be described as having an upper end 24, lower end 26 and an interior compartment 28. As seen in the drawings, guard 18 is provided with a tapered portion 30 at its lower end which is adapted to engage the beveled portion 32 in the stand 12 as illustrated in FIG. 1 to limit the inward movement of the guard 18 relative to the stand 12. Guard 18 is also provided with an elongated opening 34 extending therethrough adjacent the upper end thereof adapted to receive one end of a spring locking device 36 secured to the guard 18. As illustrated in FIG. 7, guard 18 is also provided with an opening 38 at its lower end.

For purposes of description, barrel 20 will be described as having an upper end 40 and lower end 42. As seen in FIG. 5, barrel 20 is provided with a tapered portion 44 adjacent its lower end and an opening 46 which communicates with an interior compartment 48. Barrel 20 has an annular flange 50 at its upper end and an annular groove 52 formed therein below the upper end. As seen in FIG. 4, barrel 20 is also provided with a beveled portion 54.

Plunger 22 comprises a plunger rod 55 having a tip base 56 threadably secured to the lower end thereof. As seen in FIG. 8, tip base 56 generally comprises a beveled annular portion 58 and an inverted U-shaped support 60. Opening 62 extends through the annular portion 58 as also illustrated in FIG. 8. Tip 64 is secured to the tip base 56 as illustrated in FIG. 7. As seen in FIG. 8, the reduced diameter portion 66 of tip 64 is adapted to be received by the opening 62 with the annular shoulder or flange 68 adapted to be positioned adjacent the lower end of the tip base 56. Both tip base 56 and tip 64 are preferably comprised of an electrolitic tough pitch copper. Compartment 70 extends downwardly into tip 64 to provide a lower end portion 72 on the tip 64 which preferably has a thickness of 0.005 inches.

Plunger rod 55 is provided with an elongated bore 74 which extends downwardly from the upper end thereof as illustrated in FIG. 6. A plurality of spaced apart openings 78 are provided in the upper end of the plunger rod 55 while a plurality of spaced apart openings 80 are formed in the plunger rod at the lower end of the bore 74. Flange 82 extends outwardly from plunger rod 55 to define a shoulder 84 thereabove and a shoulder 86 therebelow. A plurality of spaced apart openings 88 extend upwardly through the flange 82 as also illustrated in FIG. 6. The outer end of flange 82 is provided with threads 90 which are adapted to threadably receive the threads of the cap referred to generally by the reference numeral 92. Cap 92 is provided with an interior compartment 94 having an upper end 96 and a shoulder 98 which is adapted to engage the flange 82 to limit the relative threadable rotation therebetween. Compartment 94 is filled with a filter material 100 such as cotton or the like. Screw 102 threadably extends inwardly through the cap 92 and into the flange 82 to prevent undesirable rotation therebetween. A spring 104 embraces plunger rod 55 between shoulder 106 and collar 108 which is secured to the plunger rod by any convenient means. As seen in FIG. 6, the lower end of collar 106 engages the shoulder 110. Spring 104 normally urges plunger rod 55 upwardly relative to barrel 20 so that the beveled annular portion 58 seats upon the lower end of barrel 20 to close the opening 44.

During periods of non-use, the device 10 would normally be stored in the support 12 with the barrel 20 being received by the guard 18 and being maintained therein by the spring locking device 36 extending through the opening 34 in guard 18 and being received by the annular channel or groove 52 formed in barrel 20. When it is desired to utilize the probe of this invention, the barrel 20 is removed from the guard 18 by causing the spring locking device 36 to be moved outwardly from engagement with the groove 52 so that the barrel 20 may be vertically moved with respect to the guard 18. The guard 18 is left in the stand 12 at this time as illustrated in FIG. 3. The barrel 20 is then inserted into the bottle 14 through the opening 112 at the upper end thereof to cool the barrel slowly. Flange 50 engages the upper end of the bottle 14 to maintain the barrel in position so that the tip 64 is maintained above the lower end of the bottle 14. The barrel 20 remains in the bottle 14 until the treatment procedure commences.

When the physician desires to actually use the probe, the barrel 20 is removed from the bottle 14 for approximately thirty seconds to permit the barrel to warm slightly. The barrel 20 is then inserted in the bottle 14 with the warm barrel 20 causing the liquid nitrogen to boil. As the liquid nitrogen is boiling, the cap 92 is moved downwardly relative to the barrel 20 which causes the plunger rod 55 to move downwardly relative to the barrel 20 whereby moving the valve means 114 (comprised of tip base 56 and tip 64) so that the liquid nitrogen may by-pass the valve means 114 and to move upwardly into the interior compartment 48 as illustrated in FIG. 5. The liquid nitrogen boiling within the bottle 14 creates pressure within the bottle 14 above the liquid 16 so that pressure is exerted on the liquid 16 to aid in forcing the liquid upwardly into the interior compartment 48.

When the interior compartment 48 has been filled, (approximately one ounce) the physician releases his grasp on the cap 92 so that the spring 104 urges the plunger rod 55 upwardly relative to the barrel 20 so that valve means 114 closes the opening 46 to maintain the liquid nitrogen within interior compartment 48. The barrel 20 is then immediately placed within the guard 18 and secured therein by means of the locking device 36 as previously described. The probe is then maneuvered so that the lower end 72 of the tip 64 is placed into intimate engagement with the skin of the patient referred to generally by the reference numeral 116. The extreme thinness of the lower end portion 72 of tip 64 permits the liquid nitrogen to be closely positioned adjacent the skin so that the heat from the skin causes the liquid nitrogen to vaporize. The evaporation of the liquid nitrogen causes gas to pass upwardly in the compartment 48 and to enter the bore 74 through the openings 80. The gas passes outwardly through the openings 78 into the filter material 100. Excess gas may pass from the filter compartment 94 outwardly to the atmosphere through the openings 88 as illustrated in FIG. 6.

It is extremely important to note that a longer treatment period is achieved through the use of the cryogenic probe of this invention since the liquid nitrogen is not exposed to the atmosphere during the treatment period but still is maintained in close proximity to the skin so as to utilize the heat of the skin to vaporize the liquid nitrogen. Inconventional treatment methods, the liquid nitrogen is exposed to the atmosphere and would completely vaporize in approximately one or two seconds. With the instant invention, it is possible to maintain the tip 64 in contact with the area to be treated on the skin for approximately one minute before the liquid nitrogen has vaporized. It should be understood that the tip 64 could have any configuration so as to treat different areas but it is important that the lower end portion 72 be extremely thin.

After the skin has been treated in the desired manner, the assembly or device 10 may then be placed in the support 12 until it is desired to again use the device. Thus it can be seen that the invention accomplishes at least all of its stated objectives.

We claim:

1. The method of treating an area of a patient's skin, comprising the steps of:

providing a cryogenic probe having an interior compartment normally closed by a movable valve means which has a hollow lower end portion positioned below the probe, the interior of said valve means being in communication with said interior compartment, immersing the lower end of said probe in a cryogenic liquid, opening said valve means to introduce the cryogenic liquid into said interior compartment and to the interior of said valve means, closing said valve means, removing the probe from the cryogenic liquid container, and placing the lower end portion of said valve means into intimate contact with the area to be treated so that the heat of the patient's skin is conducted through the lower end portion of said valve means to cause the vaporization of the cryogenic liquid within the probe.

* * * * *